United States Patent [19]

Beck et al.

US005756072A

[11] Patent Number: 5,756,072
[45] Date of Patent: May 26, 1998

[54] ALKYLPOLYGLYCOSIDES WITH A HIGH DEGREE OF A POLYMERIZATION AND A PROCESS FOR THE PREPARATION THEREOF

[75] Inventors: Roland Herwig Friedrich Beck. Everberg; Myriam Elseviers. Kampenhout; Martine Maria Roberta Van Havere, Bertem, all of Belgium

[73] Assignee: Cerestar Holding B.V., Sas Van Gent, Netherlands

[21] Appl. No.: 587,677

[22] Filed: Jan. 17, 1996

[30] Foreign Application Priority Data

Jan. 18, 1995 [GB] United Kingdom .................. 9500886

[51] Int. Cl.$^6$ .............................. C07H 1/06; C07H 15/04; C07G 3/00; C08B 37/00
[52] U.S. Cl. ........................ 424/49; 424/65; 424/70.1; 424/70.13; 424/70.19; 510/127; 510/131; 510/135; 510/137; 510/151; 510/159; 510/470; 510/535; 536/1.11; 536/4.1; 536/18.6; 536/124; 536/126; 536/127
[58] Field of Search ...................... 536/18.6, 4.1, 536/144, 126, 121, 1.11, 124, 127; 424/49, 65, 70.1, 70.13, 70.19; 570/127, 131, 135, 137, 151, 159, 470, 535

[56] References Cited

U.S. PATENT DOCUMENTS 5,266,690   11/1993   McCurry et al. ............... 536/18.6
5,449,763   9/1995   Wulff et al. ................... 536/18

FOREIGN PATENT DOCUMENTS 0 249 013   12/1987   European Pat. Off. .
90/06933    6/1990    WIPO .
93/07160    4/1993    WIPO .
93/24504    12/1993   WIPO .

OTHER PUBLICATIONS

Starke, vol. 45, No. 8, 1993 Weinheim De., pp. 281–288, Biermann M. et al "Alkylpolyglucoside–Technologie und Eigenschaften".

*Primary Examiner*—Elli Peselev
*Attorney, Agent, or Firm*—Cushman Darby & Cushman IP Group of Pillsbury Madison & Sutro, LLP

[57] ABSTRACT

The present invention relates to a process for preparing alkylpolyglycoside compositions. Specifically the process is a direct synthesis producing compositions of highly polymerized alkylpolyglycosides in high yield. The invention further relates to alkylpolyglycoside compositions having enhanced surfactant properties. The invention also relates to mixtures of alkylpolyglycosides of preselected average alkyl chain length and controlled average degree of polymerization ($\overline{DP}$).

15 Claims, No Drawings

ALKYLPOLYGLYCOSIDES WITH A HIGH DEGREE OF A POLYMERIZATION AND A PROCESS FOR THE PREPARATION THEREOF

The present invention relates to a process for preparing alkylpolyglycoside compositions. Specifically the process is a direct synthesis reaction producing compositions of highly polymerized alkylpolyglycosides in high yield. The invention further relates to alkylpolyglycoside compositions having enhanced surfactant properties. The invention also relates to mixtures of alkylpolyglycosides of preselected average alkyl chain length and controlled average degree of polymerization ($\overline{DP}$).

BACKGROUND OF THE INVENTION

Throughout this specification the following definitions will be adhered to $\overline{DP}$=number average degree of polymerisation of carbohydrate bound to fatty alcohol, which is equivalent to the molar ratio of bound carbohydrate:fatty alcohol exemplified by glucose and mannose as carbohydrate.

molar ratio alcohol:carbohydrate=ratio of the two reactants used during the synthesis of APG Glu=glucose=D-glucose (glucose not in the definition as glucose syrup, but as the chemical) dextrose=as crystalline α-D-glucose.

Alkylpolyglycosides are produced by reacting a suitable carbohydrate with a fatty alcohol. A well-known example of such a reaction is the formation of alkylpolyglucosides.

Alkylpolyglucosides (APG) are produced by reacting dextrose (anhydrous, monohydrate, or high Dextrose syrups) with an excess of fatty alcohol. The amount of fatty alcohol is usually expressed as the molar ratio alcohol:dextrose. Typically this ratio lies between 3 and 6. Reacting dextrose in the presence of an acid catalyst under essentially anhydrous conditions with fatty alcohols results primarily in the following reactions:

1. Glu+ROH→RO-Glu+$H_2O\uparrow$
2a. nGlu+RO-Glu→RO-(Glu)$_{n+1}$+n$H_2O\uparrow$
2b. RO-Glu+nRO-Glu→RO-(Glu)$_{n+1}$+nROH
3a. Glu+nGlu→(Glu)$_{n+1}$+n$H_2O\uparrow$
3b. Glu+nRO-Glu→(Glu)$_{n+1}$+nROH The reactions 1 and 2 lead to the desired APG, in particular reactions 2a and 2b produce alkyloligoglucosides, whereas reactions 3a and 3b yield non surface active byproducts, the so-called polydextroses or polyglucoses.

The degree of polymerisation of an APG is dependent on the molar ratio alcohol:dextrose used. In theory an indefinite excess of alcohol would yield exclusively alkylmonoglucoside, on the other side by lowering the ratio alcohol:dextrose a lower level of the monoglucoside fraction will be obtained, and according to reaction 2a a higher level of higher DP alkyloligoglucosides.

Higher DP alkyloligoglucosides show desirable surfactant properties. Unfortunately there are technical limits to the use of lower ratios than 2–3 (alcohol:dextrose), i.e. the product can not be stirred effectively, due to too high a viscosity, which is very important in a heterogenous reaction such as APG synthesis, insufficient stirring results in the overproportional formation of the byproduct polydextrose according to reaction 3. The yield in higher DP alkyloligoglucosides is very low.

Already in the early nineteen seventies the idea of varying the $\overline{DP}$ of APGs was expressed. Processes yielding products with $\overline{DP}$ values of up to 9 or even higher were reported in the scientific and patent literature. However the processes disclosed to produce such high $\overline{DP}$ APGs do not result in the claimed products. From todays more sophisticated analytical point of view these products were poorly characterised and the products $\overline{DP}$ values were overestimated.

Two types of reactions have to be considered here in particular, A) direct synthesis of APG with a low fatty alcohol:dextrose ratio (U.S. Pat. No. 3,839,318); B) synthesis in presence of reactive solvents such as substituted glycols, using as well a low fatty alcohol:dextrose ratio (U.S. Pat. No. 3,707,535).

A) By lowering the ratio alcohol:dextrose during the reaction, an overproportionally high amount of polydextrose is formed (processing problems, too high viscosity of the slurry, too slow water removal). Only the bound alcohol or even more simply the weight yield of APG was used for $\overline{DP}$ determination. As glucosidation yields products with a higher molecular weight, in principle the increase in weight relative to the starting dextrose weight is proportional to the amount of bound fatty alcohol. This holds however only true at quantitative conversion and 100% selectivity towards APG formation.

In both analytical procedures the polydextrose is not distinguished from 'true' APG and is therefore increasing the apparent, but false, $\overline{DP}$ of the APG.

B) By reacting dextrose with low ratios of fatty alcohol in the presence of low molecular weight glycols the processing problems described under A are overcome. But as the low molecular weight glycols do also react with the dextrose it is unlikely that the glycols are again quantitatively liberated and removed during the course of the reaction. Basically the same error occurs as in A) when simply analysing the bound fatty alcohol in the APG or by weight increase determination, as the remaining glycolglucosides contribute to a wrong high DP.

In conclusion no direct synthesis for high $\overline{DP}$ APGs, when analysed with state of the art analytical methods, exists so far.

Two indirect ways of preparation have been described in the literature. The first was the fractionation with acetone (Hughes and Lew, JAOCS 47(1970) 162–167) which takes advantage of the different solubility of the higher $\overline{DP}$ fraction compared with the monoglucoside fraction. More recently an alternative process for preparing high $\overline{DP}$ APGs has been disclosed (WO 93/07160). It is based on high vacuum distillation (molecular distillation). At pressures as low as $10^{-3}$ mbar and temperatures of about 240° C. the alkyl monoglucoside becomes volatile and can be removed. The non-volatile residue is enriched with the higher $\overline{DP}$ APGs. In both cases more than 50% of the total weight (monoglucoside level of a standard APG with $\overline{DP}$=1.3 is about 65%) has to be removed to come to $\overline{DP}$ values around 1.8–2.0.

The resulting low yield and therefore high cost is clearly a big disadvantage for both processes. The latter process also suffers from extreme processing conditions which are further very difficult and expensive to be realised on a technical scale.

One type of APGs, with a $\overline{DP}$ of 1.25–1.4 (depending on the analytical method used) is presently available. Only the hydrophobic chain length is subject to variation. Concerning the application potential of APGs a variable $\overline{DP}$ greatly enlarge its use. In a similar way as for alcohol ethoxylates APGs then cover a wide range of HLB values, and use cheaper hydrophobic moieties, e.g. the $C_{16}$–$C_{18}$ fatty alcohol cut. APGs with different $\overline{DP}$ values also perform differently in applications, such as detergents and personal care products, in e.g. detergency, emulsification, foaming characteristics (Koeltzow & Urfer, JAOCS 61 (1984) 1651; Hughes & Lew, JAOCS 47 (1970) 162).

SUMMARY OF THE INVENTION

The present invention discloses a process for preparing high DP̄ alkylpolyglycosides by direct synthesis. The process of the present invention comprises the following steps:

a) an alkylpolyglycoside is prepared by reacting a carbohydrate with an excess of fatty alcohol in the presence of an acid catalyst in solution, b) the solution is subjected to a first evaporation step (without prior neutralisation) until the remaining alcohol is in the range of 5–40% (w/w), c) the alkylglycoside/fatty alcohol solution of step b) is incubated at a temperature above the clearing point of the liquid crystalline alkylpolyglycoside/fatty alcohol system for a desired time, d) the solution of step c) is neutralized, e) the neutralized solution of step d) is subjected to a second evaporisation and subsequently optionally bleached.

The present invention discloses a process for preparing high DP̄ alkylpolyglucosides by direct synthesis. The process of the present invention comprises the following steps:

a) an alkylpolyglucoside is prepared by reacting a dextrose with an excess of fatty alcohol in the presence of an acid catalyst in solution, b) the solution is subjected to a first evaporation step (without prior neutralisation) until the remaining alcohol is in the range of 5–40% (w/w), c) the alkylglucoside/fatty alcohol solution of step b) is incubated at a temperature above the clearing point of the liquid crystalline alkylpolyglucoside/fatty alcohol system for a desired time, d) the solution of step c) is neutralize, e) the neutralized solution of step d) is subjected to a second evaporisation and subsequently optionally bleached.

The process of the present invention yields an alkylpolyglycoside composition characterized by a high degree of polymerisation.

The present invention is exemplified by the use of glucose as a starting carbohydrate.

The present invention therefore discloses an alkylpolyglucoside composition containing a high amount of highly polymerized alkylpolyglucosides, preferably with a DP̄>1.8 and wherein the percentage of DP4 and higher is more than 20%. The alkylpolyglucoside compositions of the present invention are further characterized by containing less than 20% of polydextrose based on the non-volatile residue.

DETAILED DESCRIPTION OF THE INVENTION

The present invention relates to a process for preparing high DP̄ alkylpolyglycosides by direct synthesis. This process distinguishes from the known processes in that the level of non surface active by-products (polydextroses) is relatively low when compared with known direct synthesis methods and in that the overall yield in high DP alkylpolyglycosides is relatively high when compared with known indirect synthesis methods.

Carbohydrates, used for the glycosidation reaction to produce alkyl polyglycosides include hexoses, i.e. glucose, mannose, allose, altrose, galactose, talose, gulose, idose, fructose, psicose, tagatose, sorbose, as well as pentoses, i.e. ribose, arabinose, xylose, lyxose, ribulose, xylulose, and deoxycarbohydrates, e.g. rhamnose, fucose, and mixtures thereof. Such mixtures are obtained by hydrolysis of di-, oligo-, and polysaccharidic materials, respectively, for instance a glucose/fructose mixture from sucrose, or a galactose/glucose mixture from lactose or even a complex mixture of monosaccharides obtained from the hydrolysis of hemicellulosic or pectic materials or plant gums. Monosaccharide mixtures useful for the glycosidation reactions are also manufactured on purpose, for instance high fructose syrups via enzymatic isomerisation, or mannose containing syrups via molybdate or nickel catalysed epimerisation.

The present invention is examplified by the use of glucose the other carbohydrates mentioned above give similar results.

Therefore the invention provides a fast and economical process for obtaining high DP̄ alkylpolyglucosides. The invention further provides high DP̄ alkylpolyglucoside compositions.

These compositions contain higher DP alkylpolyglucosides in increased amounts as compared with known APG compositions. Furthermore the amounts are varied by simple alteration of process parameters. In order to obtain the above compositions the present invention provides a new process.

The process for preparing high DP̄ alkylpolyglucosides of the present invention is characterized by the followings steps:

a) an alkylpolyglucoside is prepared by reacting a dextrose with an excess of fatty alcohol in the presence of an acid catalyst in solution, b) the solution is subjected to a first evaporation step (without prior neutralisation) until the remaining alcohol is in the range of 5–40% (w/w), c) the alkylglucoside/fatty alcohol solution of step b) is incubated at a temperature above the clearing point of the liquid crystalline alkylpolyglucoside/fatty alcohol systems for a desired time, d) the solution of step c) is neutralized, e) the neutralized solution of step d) is subjected to a second evaporisation and subsequently optionally bleached.

The alkylpolyglucoside is prepared in a standard way (step a) ) i.e. by reacting a dextrose with an excess of a fatty alcohol in the presence of an acid catalyst. This step of the process is known from the prior publications for example from U.S. Pat. Nos. 3,707,536 and 3,839,318.

Briefly, a higher alcohol is reacted with dextrose in a molar ratio of from 6 to 1 down to 1 to 1 preferably of from 4 to 1 down to 1.25 to 1. If less than one mol of alcohol/mol of dextrose is employed the reaction mixture becomes too viscous leading to an inhomogeneous solution and therefore to an inhomogeneous product. When molar ratios above 6 are employed the required reaction volume becomes too large, leading to productivity loss per unit of reactor volume.

For the detergent/surfactant use application the alcohol employed is preferably monohydric and contains from 8 to 20 carbon atoms. While the preferred alcohol contains saturated aliphatic or alkyl chains, some unsaturated aliphatic groups may be present. Fatty alcohols that can be employed are derived from the naturally occurring fats and oils examples are n-octanol, n-decanol, n-dodecanol, n-tetradecanol, n-hexadecanol, n-octadecanol, oleol, linoleol. Synthetically produced Ziegler alcohols or oxo-alcohols (branched alcohols) with from 8 to 18 carbon atoms can also be employed.

The fatty alcohol/dextrose reaction is performed at a temperature between 80° C. and 130° C., preferably between 90° and 120° C.

The reaction is performed using an acid catalyst, suitable catalysts include strong inorganic acids, sulfuric acid, hydrochloric acid, nitric acid etc., strong organic acids and acid ion exchange resins.

This reaction step typically leads to an APG having $\overline{DP}$ between 1.2 and 1.7 depending on the molar ratio employed, in a fatty alcohol solution. On a weight basis the mixture contains about 30% APG and 70% fatty alcohol.

In the known APG processes this solution is neutralised and the excess fatty alcohol is removed by a continuous two stage vacuum evaporation until the remaining alcohol is below 1%. Finally the product is bleached.

The process of the present invention differs from the known processes essentially in that the APG/fatty alcohol solution is not neutralised prior to the first stage evaporation and that the fatty alcohol is not quantitatively removed. After the first evaporation 5 to 40% fatty alcohol remains in the product.

The non-neutralised APG/fatty alcohol solution is further incubated for a desired time at a temperature above the clearing point of the liquid crystalline APG/fatty alcohol system. Under these conditions transglucosidation (reaction 2b, above) takes place yielding higher $\overline{DP}$ APG and more free fatty alcohol. The incubation is continued until $\overline{DP}$ of the APG is larger than 1.6 preferably larger than 1.8. Finally, the product is neutralized and the alcohol is removed in the second stage of evaporisation using standard methods.

The alkylpolyglucoside composition obtained with the process of the present inventions contains a high amount of highly polymerized APG, preferably with a $\overline{DP}>1.8$ and wherein the percentage of DP4 and higher is larger than 20%. The product is further characterized in that the amount of polydextrose is less then 20% based on the non-volatile residues. The alkylpolyglucoside composition is for example used in a hard surface cleaner, a detergent (laundry, dish wash) a liquid handsoap and shampoo.

The reaction product of glucose and fatty alcohol in the presence of an acid catalyst results in a mixture of a monoglucoside of the alcohol and various higher degrees of polymerization polyglucosides. The higher polyglucosides are present in decreasing amounts i.e. DP2>DP3>DP4 etc. Such a distribution is called a Schulz=Flory distribution.

The process of the present invention leaves the distribution intact, however $\overline{DP}$ is increased.

In order to obtain a higher $\overline{DP}$ and therefore more of the higher $\overline{DP}$ APG, WO 93/07160 describes molecular distillation. In this case the monoalkylglucoside is removed.

This leads to two products a alkylmonoglucoside and a mixture of alkylmono- and alkylpolyglucosides. Overall the distillation does not increase the yield in higher alkylpolyglucosides however the process is very expensive from an investment and energetic point of view.

The process of the present invention gives an increased yield of higher APGs at a lower processing energy and investment cost.

The difference can be illustrated as follows.

The product obtained in our process is different from the products obtained by molecular distillation/fractionation of a standard $\overline{DP}$ APG as obtained for example in international patent application WO 93/07160. Separation of the monoglucoside fraction from the rest leaves the proportion of DP2 to DP3 and DP4 unchanged as it is found in the original APG. In the process of the present invention the amounts of higher DP APGS changes due to a decrease in the amount of monoglucoside, i.e. a part of the mono glucoside is converted to alkyloligoglucosides. A typical example for a dodecyl-APG, where the $\overline{DP}$ has been increased by evaporation of the monoglucoside fraction, at a recovery rate of the non-volatile fraction (=high $\overline{DP}$ APG) of 42.7%, is as follows:

|       | Starting distribution [%] | After DP1 removal [%] | After DP1 removal (normalised) [%] |
|-------|---------------------------|-----------------------|-------------------------------------|
| DP1   | 67.3                      | 10.0                  | 23.4                                |
| DP2   | 22.9                      | 22.9                  | 53.6                                |
| DP3   | 7.0                       | 7.0                   | 16.4                                |
| DP4   | 2.0                       | 2.0                   | 4.7                                 |
| DP5   | 0.5                       | 0.5                   | 1.2                                 |
| DP6+  | 0.3                       | 0.3                   | 0.7                                 |
| $\overline{DP}$ | 1.30            |                       | 1.88                                |

Applying the process of the present invention the product distribution looks as follows:

|       | Starting distribution [%] | After incubation [%] |
|-------|---------------------------|----------------------|
| DP1   | 67.3                      | 37.4                 |
| DP2   | 22.9                      | 25.8                 |
| DP3   | 7.0                       | 16.0                 |
| DP4   | 2.0                       | 9.4                  |
| DP5   | 0.5                       | 5.3                  |
| DP6+  | 0.3                       | 6.1                  |
| $\overline{DP}$ | 1.30            | 1.88                 |

Comparing the two processes it is clear that at the same $\overline{DP}$ the distribution of the individual alkyloligoglucosides is very different. In our process the proportion of DP4 and higher DPs is strongly increased compared with the product obtained by molecular distillation.

As in the process of the present invention only alcohol is released, which is easily recycled into further APG production, no recovery reductions as in the molecular distillation/fractionation processes are occurring.

EXAMPLES

Example 1

APG was produced in a standard way (as e.g. specified in U.S. Pat No. 3,839,318) using a molar ratio dodecanol:dextrose=5:1, resulting in an APG of $\overline{DP}$=1.26. The product had the following composition: 71.9% dodecanol and 28.1% non-volatile residue consisting of 99.4% APG ($\overline{DP}$=1.26), 0.4% polydextrose and 0.2% p-toluenesulfonic acid.

1415.6 g of this APG solution were evaporated in a short path evaporator (UIC KDL 4) at a feeding rate of 35 ml/min applying a vacuum of 9–10 mbar. The APG solution and the pump head was thermostated to 80° C., the evaporator temperature was 165° C. The condensor temperature was set to 40° C. The speed of the wipers was 375 rpm. 959.5 g of clear dodecanol was recovered in the volatile phase. 456.1 g of non-volatile residue was obtained. Calculating the mass balance of the evaporation step the obtained product consists nominally of 87.3% APG ($\overline{DP}$=1.26) and 12.7% dodecanol. In practice however some transglycosidation will have taken place already in the evaporator, resulting actually in a higher $\overline{DP}$ and a higher amount of free dodecanol (Reaction 2b).

The 456.1 g of non-volatile residue were further reacted under stirring at 100° C. for 1 hour, and then neutralised with the appropriate amount of magnesium hydroxide. The product had the following composition: 33.1% dodecanol, 66.9% of non-volatile residue consisting of 96.6% APG, 2.2% polydextrose and 1.2% magnesium p-toluenesulfonate. The product before and after reaction, respectively, had the following DP-distribution (determined by HPLC):

|      | after reaction [%] | starting material [%] |
|------|--------------------|-----------------------|
| DP1  | 31.0               | 70.8                  |
| DP2  | 24.0               | 21.4                  |
| DP3  | 16.7               | 5.8                   |
| DP4  | 11.0               | 1.5                   |
| DP5  | 7.0                | 0.4                   |
| DP6+ | 10.3               | 0.1                   |
| $\overline{DP}$ | 2.10    | 1.26                  |

The product was worked up according to the state of the art APG production, i.e. evaporation of the alcohol, dissolution in water and bleaching to yield an almost colourless aqueous APG solution, exhibiting significantly higher solubility and solution stability than the APG ($\overline{DP}$=1.26) presently available.

Example 2

Performed as Example 1 with the exception of the starting material (starting ratio fatty alcohol:dextrose 3.8:1 yielding an APG with a $\overline{DP}$=1.33 and a polydextrose content of 5.5% based on the non-volatile residue), and varying the reaction temperature as a function of the reaction time. The dodecanol remaining nominally in the non-volatile residue after evaporation was 37.9% (evaporation conditions as in Example 1 with the exception of the vacuum, which was set to 16 mbar). The development of the $\overline{DP}$ and polydextrose formation is given in Table 1:

TABLE 1

| Temperature [°C.] | Reaction Time [min] | $\overline{DP}$ | Polydextrose [%] |
|-------------------|---------------------|-----------------|------------------|
| 100               | 0                   | 1.33            | 5.5              |
|                   | 20                  | 1.75            | 7.3              |
|                   | 35                  | 1.85            | 8.5              |
|                   | 50                  | 1.96            | 10.3             |
|                   | 90                  | 1.99            | 13.8             |
| 105               | 0                   | 1.33            | 5.5              |
|                   | 20                  | 1.86            | 8.4              |
|                   | 35                  | 1.91            | 8.9              |
|                   | 50                  | 1.98            | 11.0             |
|                   | 90                  | 1.98            | 15.6             |
| 110               | 0                   | 1.33            | 5.5              |
|                   | 20                  | 1.81            | 7.5              |
|                   | 35                  | 1.91            | 8.1              |
|                   | 50                  | 1.98            | 9.2              |
|                   | 90                  | 1.97            | 12.6             |

Example 3

As Example 1 with the exception that octyl-APG was used (starting molar ratio octanol:dextrose=5:1, $\overline{DP}$=1.23 and a polydextrose content of 0.5% based on the non-volatile residue). Evaporation conditions were as in Example 1 with the exception of evaporation temperature (100°–130° C.) and vacuum (4–20 mbar). The nominal residual alcohol present during further reaction at constant reaction temperature (100° C.) was varied. Table 2 gives the evolution of the $\overline{DP}$ and the polydextrose as a function of reaction time.

TABLE 2

| Amount Octanol [%] | Reaction Time [min] | $\overline{DP}$ | Polydextrose [%] |
|--------------------|---------------------|-----------------|------------------|
| 9.3                | 0                   | 1.23            | 0.5              |
|                    | 15                  | 1.96            | 1.9              |
|                    | 30                  | 2.18            | 3.3              |
|                    | 45                  | 2.34            | 5.0              |
|                    | 60                  | 2.40            | 6.2              |
|                    | 90                  | 2.44            | 10.8             |
|                    | 135                 | 2.48            | 14.9             |
|                    | 210                 | 2.58            | 18.8             |
| 13.3               | 0                   | 1.23            | 0.5              |
|                    | 15                  | 1.97            | 2.2              |
|                    | 30                  | 2.17            | 3.2              |
|                    | 45                  | 2.34            | 4.4              |
|                    | 60                  | 2.45            | 6.4              |
|                    | 90                  | 2.47            | 10.3             |
|                    | 135                 | 2.52            | 11.6             |
|                    | 210                 | 2.68            | 16.3             |
| 18.3               | 0                   | 1.23            | 0.5              |
|                    | 15                  | 1.98            | 1.9              |
|                    | 30                  | 2.20            | 2.9              |
|                    | 45                  | 2.18            | 4.7              |
|                    | 60                  | 2.41            | 6.8              |
|                    | 90                  | 2.44            | 9.7              |
|                    | 135                 | 2.48            | 14.3             |
|                    | 210                 | 2.64            | 18.2             |
| 23.3               | 0                   | 1.23            | 0.5              |
|                    | 15                  | 1.88            | 1.8              |
|                    | 30                  | 2.05            | 2.6              |
|                    | 45                  | 2.09            | 3.2              |
|                    | 60                  | 2.15            | 4.1              |
|                    | 90                  | 2.23            | 5.9              |
|                    | 135                 | 2.28            | 7.9              |
|                    | 210                 | 2.34            | 12.3             |

What we claim is:

1. A process for preparing $\overline{DP}$ alkylpolyglycosides comprising the combination of steps of:
   a) preparing an alkylpolyglycoside by reacting a carbohydrate with an excess of fatty alcohol in the presence of an acid catalyst in solution,
   b) subjecting the solution to a first evaporation step, without prior neutralizing, until the remaining alcohol is in the range of 5–40% (w/w),
   c) incubating the alkylpolyglucoside/fatty alcohol solution of step b) at a temperature above the clearing point of the liquid crystalline alkylpolyglycoside/fatty alcohol system for a period of time,
   d) neutralizing the solution of step c),
   e) subjecting the neutralized solution of step d) to a second evaporization, and subsequently optionally to bleaching.

2. A process for preparing high $\overline{DP}$ alkylpolyglucosides comprising the combination of steps of:
   a) preparing an alkylpolyglucoside by reacting a dextrose with an excess of fatty alcohol in the presence of an acid catalyst in solution,
   b) subjecting the solution to a first evaporation step without prior neutralization until the remaining alcohol is in the range of 5–40% (w/w),
   c) incubating the alkylpolyglucoside/fatty alcohol solution of step b) at a temperature above the clearing point of the liquid crystalline alkylpolyglucoside/fatty alcohol system for a period of time,
   d) neutralizing the solution of step c),
   e) subjecting the neutralized solution of step d) to a second evaporization and subsequently optionally to bleaching.

3. A process according to claim 1 or 2, wherein the fatty alcohol is a monohydric straight or branched primary alcohol having from 8 to 20 carbon atoms.

4. A process according to claim 2, wherein the fatty alcohol is a monohydric straight or branched primary alcohol having from 8 to 20 carbon atoms and the molar ratio of fatty alcohol:dextrose is from 6:1 to 1:1.

5. A process according to claim 2, wherein the fatty alcohol is monohydric straight or branched primary alcohol having from 8 to 20 carbon atoms and the molar ratio of fatty alcohol:dextrose is from 4:1 to 1.25:1.

6. A process according to claim 2, wherein the molar ratio of fatty alcohol:dextrose is from 6:1 to 1:1.

7. A process according to claim 6, wherein the molar ratio of fatty alcohol:dextrose is from 4:1 to 1.25:1.

8. A process according to claim 1, wherein the molar ratio of fatty alcohol:carbohydrate is 4:1 to 1.25:1.

9. A process according to claim 8, wherein the molar ratio of fatty alcohol:carbohydrate is 4:1 to 1.25:1.

10. A process according to claim 2, wherein the alkylpolyglucoside/fatty alcohol solution is incubated (step c) for a sufficient time to obtain an alkylpolyglucoside mixture with DP>1.8 and DP4 and higher is larger than 20%.

11. A process according to claim 3, wherein the alkylpolyglucoside/fatty alcohol solution is incubated (step c) for a sufficient time to obtain an alkylpolyglucoside mixture with DP>1.8 and wherein the percentage of DP4 and higher is larger than 20%.

12. A process according to claim 4, wherein to alkylpolyglucoside/fatty alcohol solution is incubated (step c) for a sufficient time to obtain an alkylpolyglucoside mixture with DP>1.8 and DP4 and higher is larger than 20%.

13. An alkylpolyglucoside composition containing a high amount of highly polymerized alkylpolyglucosides with a DP>1.8 and wherein the percentage of DP4 and higher is larger than 20%, and said alkylpolyglucoside composition has a Flory distribution.

14. A composition according to claim 13, wherein said composition contains less than 20% of polydextrose based on the non-volatile residues.

15. A hard surface cleaner, a laundry detergent, a liquid handsoap, or a hair shampoo which comprises an alkylpolyglucoside composition according to claim 13 or 14.

* * * * *